United States Patent
Krastev

(10) Patent No.: US 9,795,467 B2
(45) Date of Patent: Oct. 24, 2017

(54) APPARATUS AND METHOD FOR SINUS LIFT PROCEDURE

(71) Applicant: Pavel Krastev, New Hyde Park, NY (US)

(72) Inventor: Pavel Krastev, New Hyde Park, NY (US)

( * ) Notice: Subject to any disclaimer, the term of this patent is extended or adjusted under 35 U.S.C. 154(b) by 1135 days.

(21) Appl. No.: 13/942,920

(22) Filed: Jul. 16, 2013

(65) Prior Publication Data

US 2014/0038126 A1    Feb. 6, 2014

Related U.S. Application Data

(60) Provisional application No. 61/674,121, filed on Jul. 20, 2012.

(51) Int. Cl.
    *A61C 19/04*      (2006.01)
    *A61C 8/00*      (2006.01)

(52) U.S. Cl.
    CPC ............ *A61C 19/04* (2013.01); *A61C 8/0092* (2013.01)

(58) Field of Classification Search
    CPC ............................. A61C 8/0092; A61C 19/04
    USPC ............................................. 433/75, 87, 144
    See application file for complete search history.

(56) References Cited

U.S. PATENT DOCUMENTS

| | | | |
|---|---|---|---|
| 4,112,944 A | 9/1978 | Williams | |
| 4,298,074 A * | 11/1981 | Mattchen | A61B 17/1624 173/129 |
| 4,412,825 A | 11/1983 | Tokarz | |
| 4,431,416 A | 2/1984 | Niznick | |
| 4,673,353 A | 6/1987 | Nevin | |
| 5,049,125 A | 9/1991 | Accaries | |
| 5,188,488 A | 2/1993 | Nakayama | |
| 5,261,818 A | 11/1993 | Shaw | |
| 5,291,914 A | 3/1994 | Bares | |
| 5,312,255 A | 5/1994 | Bauer | |
| 5,456,601 A | 10/1995 | Sendax | |
| 5,481,260 A | 1/1996 | Buckler et al. | |
| 5,575,650 A | 11/1996 | Niznick et al. | |
| 5,584,688 A | 12/1996 | Sakuma | |
| 5,685,716 A | 11/1997 | Linkow | |
| 5,711,315 A | 1/1998 | Jerusalmy et al. | |
| 5,759,036 A | 6/1998 | Hinds | |
| 5,782,918 A | 7/1998 | Klardie et al. | |

(Continued)

*Primary Examiner* — Anu Ramana
(74) *Attorney, Agent, or Firm* — Thomas A. O'Rourke; Bodner & O'Rourke, LLP

(57) ABSTRACT

An osteotome for sinus lift procedures includes a body interchangeable with various handles. The body includes a shaft that is releasably received into the handle, and a tip portion. The tip portion may be directly utilized for ridge expansion/bone compression, or a succession of tip members may instead be received thereon to provide suitable diameter escalation to create the socket. A conduit in the tip portion interconnects with a conduit in a hydration port and a conduit in a tip member. A hose couples the hydration port to a syringe, to deliver fluid out the tip member to lift the membrane. Graduated syringe markings permit delivery of measured fluid quantities to control the amount of lift. A second hydration port is coupled to a graduated cylinder through a valve, which is opened after lifting is complete, to measure the fluid released. A loss of fluid measured indicates a sinus tear.

6 Claims, 14 Drawing Sheets

(56) References Cited

U.S. PATENT DOCUMENTS

| | | | |
|---|---|---|---|
| 5,795,160 A | 8/1998 | Hahn et al. | |
| 5,829,977 A | 11/1998 | Rogers et al. | |
| 5,839,899 A | 11/1998 | Robinson | |
| 5,879,161 A | 3/1999 | Lazzara | |
| 5,915,967 A | 6/1999 | Clokie | |
| 5,967,777 A | 10/1999 | Klein et al. | |
| 5,989,025 A | 11/1999 | Conley | |
| 6,068,479 A | 5/2000 | Kwan et al. | |
| 6,117,125 A * | 9/2000 | Rothbarth | A61M 25/007 604/264 |
| 6,159,161 A | 12/2000 | Hodosh | |
| 6,171,312 B1 | 1/2001 | Beaty | |
| 6,200,289 B1 | 3/2001 | Hochman | |
| 6,273,720 B1 | 8/2001 | Spalten | |
| 6,695,847 B2 * | 2/2004 | Bianchetti | A61B 17/1688 606/53 |
| 6,758,673 B2 | 7/2004 | Fromovich et al. | |
| 7,100,476 B1 | 9/2006 | Feit | |
| 7,125,253 B2 | 10/2006 | Kitamura | |
| 7,217,130 B2 | 5/2007 | Giorno | |
| 7,297,102 B2 | 11/2007 | Smith et al. | |
| 7,364,430 B2 | 4/2008 | Kitamura et al. | |
| 7,396,232 B2 | 7/2008 | Fromovich | |
| 7,510,397 B2 | 3/2009 | Hochman | |
| 7,632,280 B2 | 12/2009 | Hochman | |
| 7,771,199 B2 | 8/2010 | Hochman | |
| 8,029,284 B2 | 10/2011 | Better | |
| 8,083,747 B2 | 12/2011 | Song | |
| 2003/0105469 A1 | 6/2003 | Karmon | |
| 2003/0175656 A1 | 9/2003 | Livne et al. | |
| 2003/0228556 A1 | 12/2003 | Giorno | |
| 2003/0232308 A1 | 12/2003 | Simmons | |
| 2006/0020326 A9 | 1/2006 | Bolduc | |
| 2006/0084034 A1 | 4/2006 | Hochman | |
| 2006/0172255 A1 | 8/2006 | Hochman et al. | |
| 2007/0042326 A1 | 2/2007 | Cardoso | |
| 2007/0055257 A1 | 3/2007 | Vaccaro | |
| 2007/0162024 A1 | 7/2007 | Siemonsmeier | |
| 2008/0215010 A1 | 9/2008 | Silver | |
| 2008/0319466 A1 | 12/2008 | Eder | |
| 2009/0042158 A1 | 2/2009 | Steiner | |
| 2009/0292288 A1 | 11/2009 | Hung | |
| 2009/0326440 A1 | 12/2009 | Lee | |
| 2010/0196841 A1 | 8/2010 | Nahlieli | |
| 2010/0221681 A1 | 9/2010 | Hochman | |
| 2010/0291511 A1 | 11/2010 | Lee | |
| 2010/0324561 A1 | 12/2010 | Watzek et al. | |

* cited by examiner (Prior Art Osteotome)

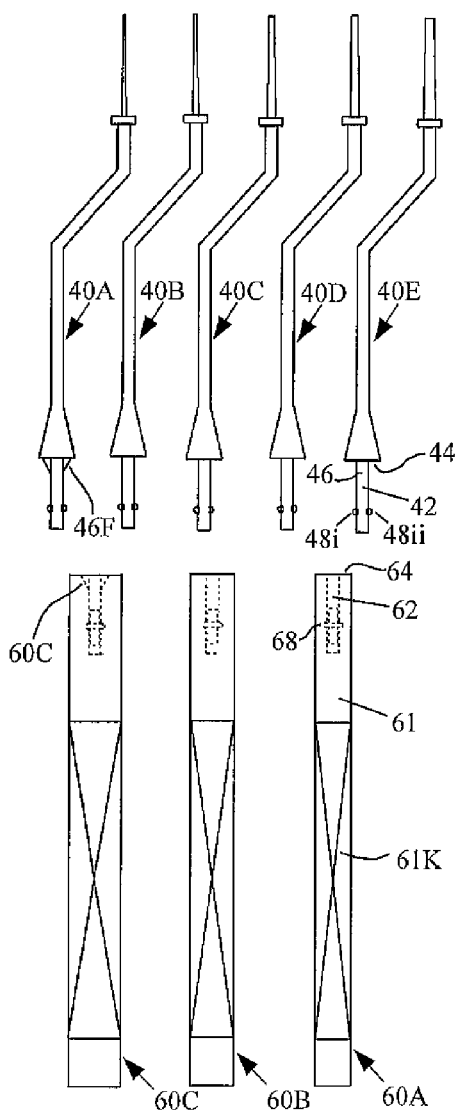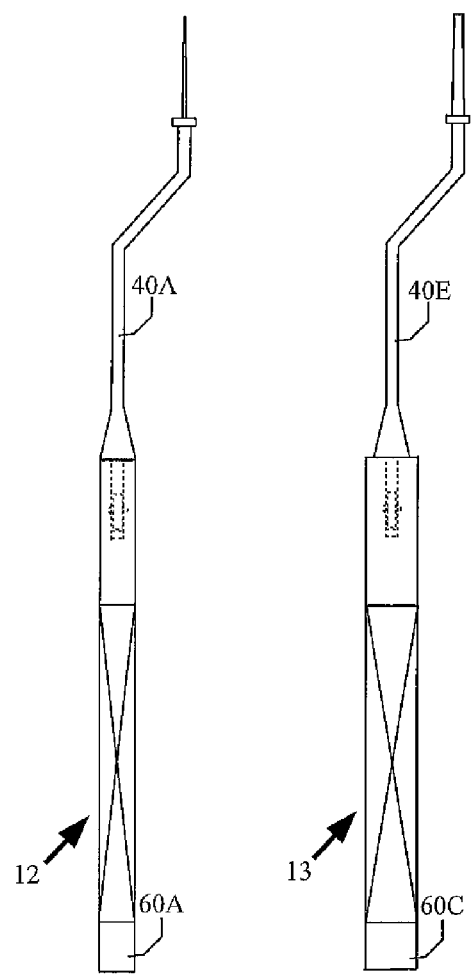
FIG. 4A  FIG. 4B  FIG. 4C

FIG. 5E  FIG. 5D  FIG. 5C  FIG. 5B

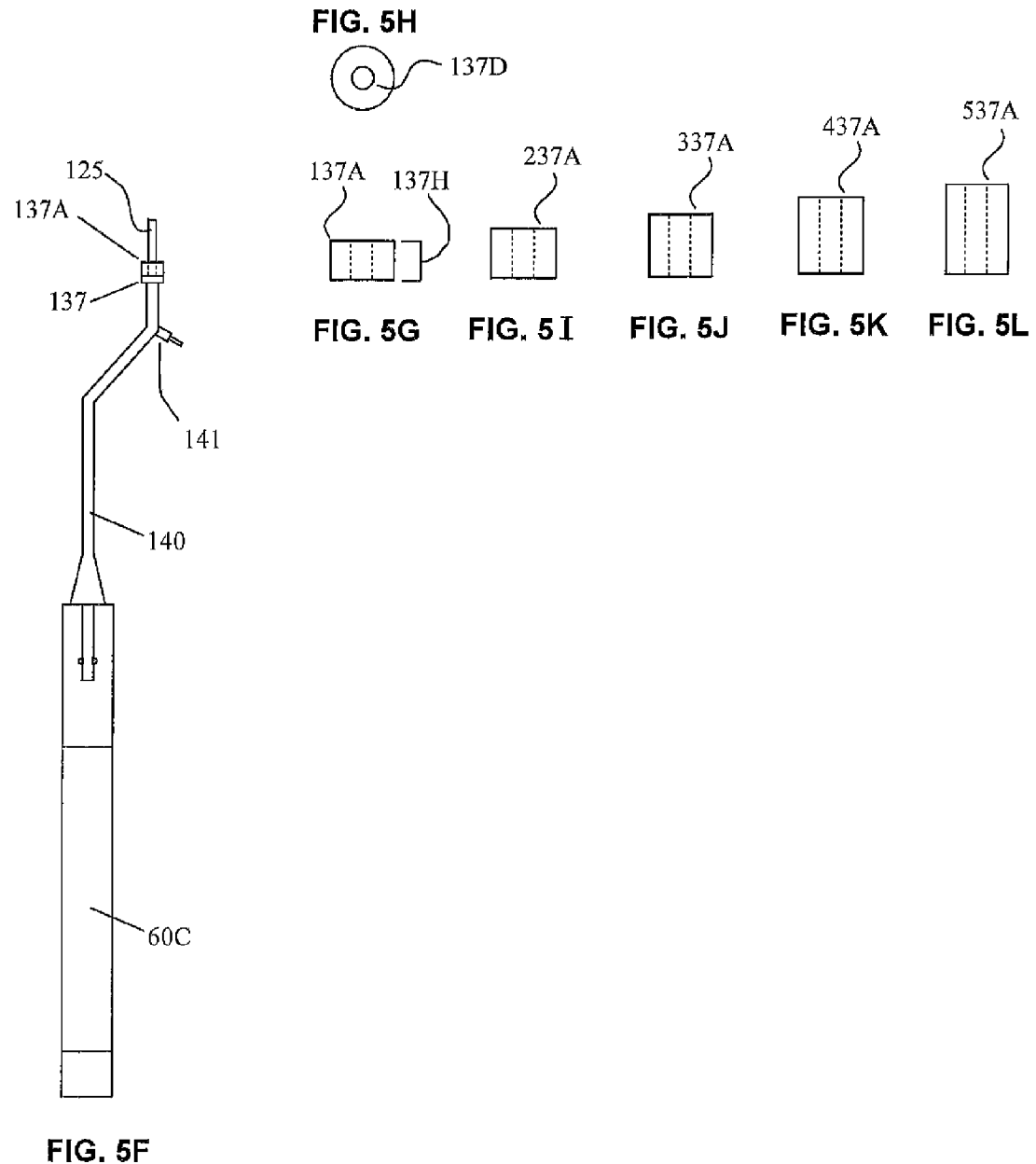

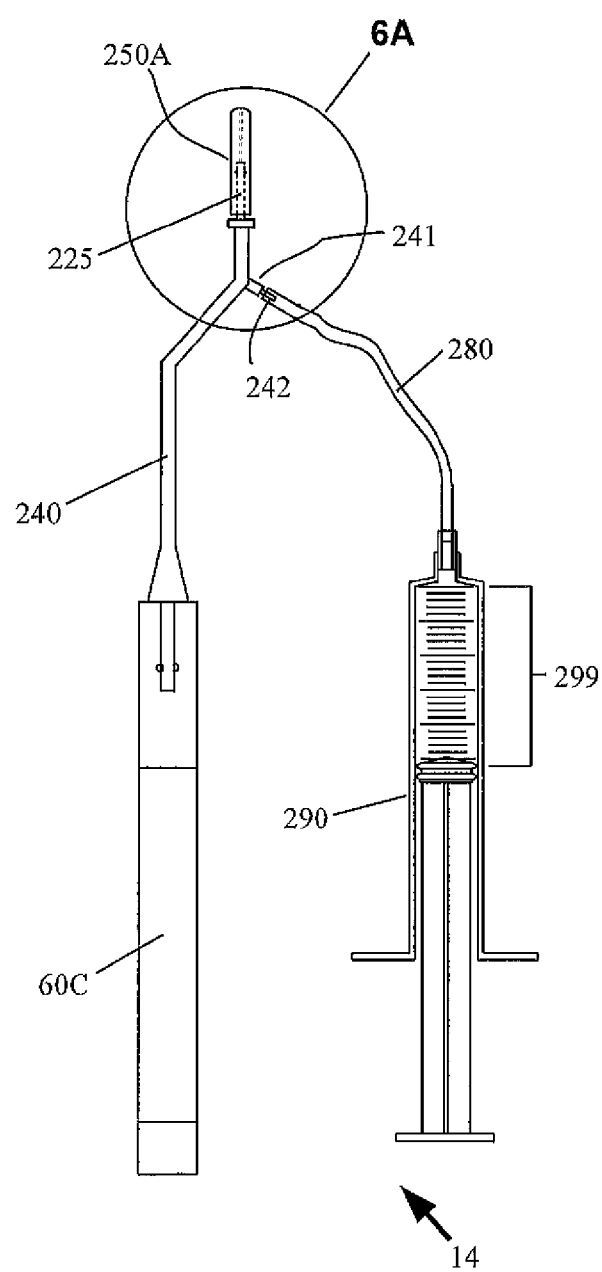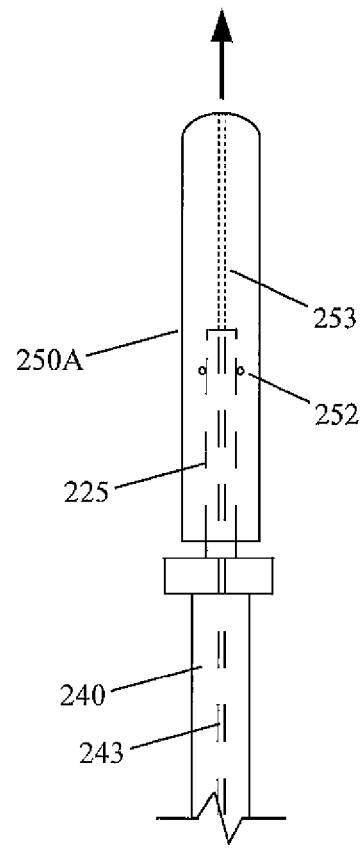
FIG. 6
FIG. 6A

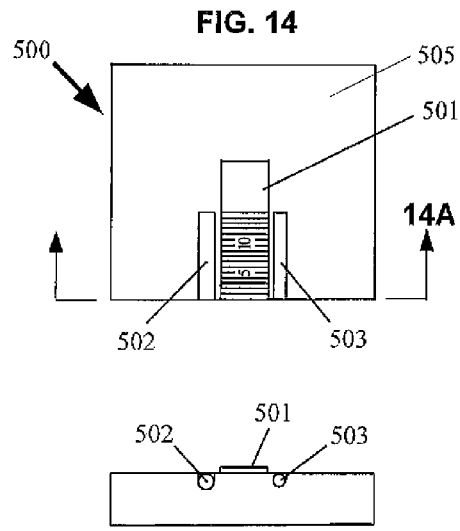
FIG. 14
FIG. 14A
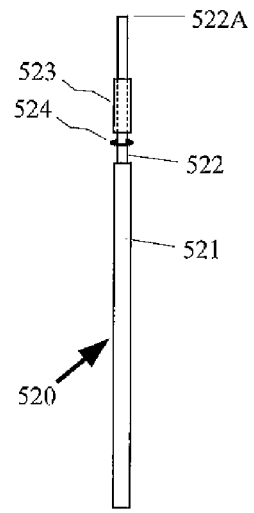
FIG. 15
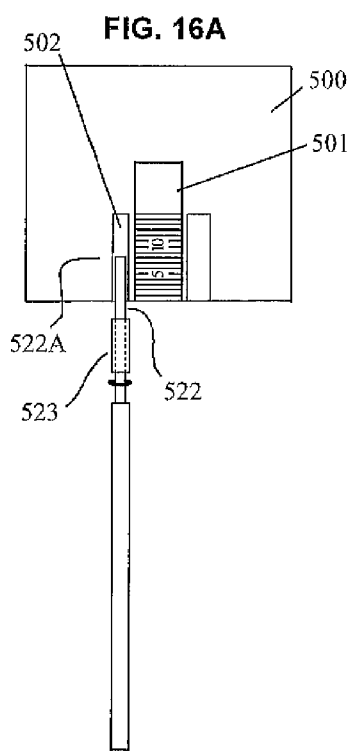
FIG. 16A
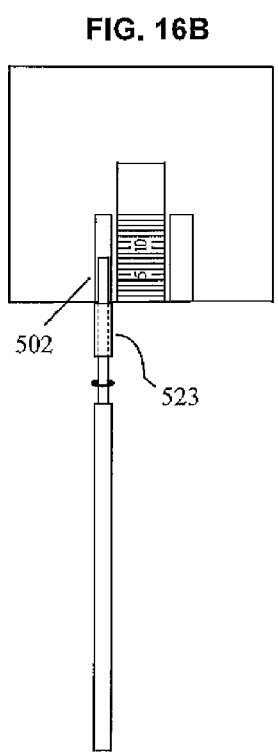
FIG. 16B
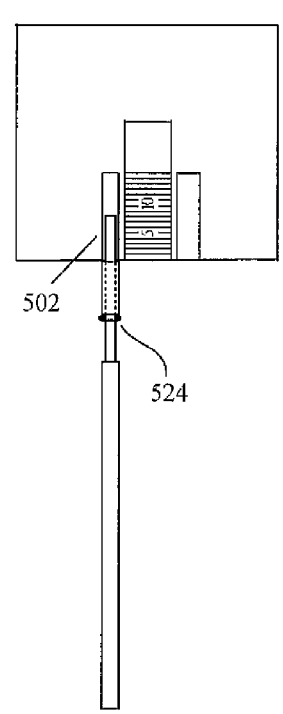
FIG. 16C

APPARATUS AND METHOD FOR SINUS LIFT PROCEDURE

CROSS REFERENCES TO RELATED APPLICATIONS

This application claims priority on U.S. Provisional Application Ser. No. 61/674,121 filed on Jul. 20, 2012, the disclosures of which are incorporated herein by reference.

FIELD OF THE INVENTION

The present invention relates to improvements in Osteotomes for performing crestal approach sinus lift procedures, and more particularly to improvements that reduce the number of separate tools that must be obtained and utilized by the dental specialist, as well as improvements that better facilitate completing the procedure more safely.

BACKGROUND OF THE INVENTION

There are many conditions which may result in a person becoming partially or completely edentulous (periodontal disease, an injury, etc.), which in the past had been remedied by the wearing of a prosthetic device, known as dentures. Dentures were constructed to replace the missing teeth and were supported by surrounding teeth and/or by the underlying tissue. The significant drawbacks to the wearing of such partial or complete dentures, principally its means of support which often required the use adhesives and its cleaning requirements, served to bolster the development of dental implants.

Dental implants may be subperiosteal, being placed on top of the bone and beneath the periostium—the fibrous membrane covering the jaw bones- and may have posts protruding through the gum to support a prosthesis. Alternatively, a dental implant may be endosteal (in the bone-endosseous), being a "root" device that is usually made of titanium, which is inserted into the jaw through the bone at the alveolar ridges. A healing period on the order of months is necessary for osseointegration, during which time the bone will grow in and around the implant to provide support that may exceed that of the natural tooth. After the healing period, an abutment may be attached thereto and may protrude through the periostium to receive a prosthodontic appliance—a new tooth. Endosteal implants are used within wide and deep bone, or bone at least wide enough for their placement. Where the jaw bone is too narrow and not a good candidate for endosseous implants, a subperiosteal implant may be utilized. However, the subperiosteal implant technique is seldom used today.

The alveolar ridges are columns of bone, found on both the maxilla and the mandible, that surround and anchor the teeth within sockets known as alveoli. However, the alveolar bone quickly becomes atrophic in the absence of teeth, resulting in lack of available bone. In the Maxilla, sinus pneumatization decreases available bone after tooth loss, requiring a sinus elevation procedure prior to implant placement. Studies have shown the bone loss to be progressive. In many cases where a patient's jaw bone may have become too shallow or narrow for an endosteal implant, a sinus lift procedure may be performed to increase the amount of bone in the maxilla. The sinus lift procedure may be performed either through a lateral approach or a crestal approach.

In the crestal approach for a sinus lift procedure of the posterior maxilla (upper jaw), to which the improvements of the present invention is directed, a pilot drill may initially be used to create a small hole to form an implant insertion axis. The depth of penetration by the drill may be limited, by a stop or guide that is set using x-rays of the crestal area, so as to be within 1-2 mm of the sinus floor. The anatomical characteristics of the posterior maxilla, particularly the existence of its more spongy (cancellous) bone, enable it to successfully lend itself to undergo the ridge expansion osteotomy technique developed by R. B. Summers, which was published in 1994 (see e.g., Summers, DMD, Robert B, "A New Concept in Maxillary Implant Surgery: The Osteotome Technique;" 1994; Summers, DMD, Robert B, "The Osteotome Technique: Part 2—The Ridge Expansion Osteotomy (REO) Procedure;" 1994; and Summers, DMD, Robert B, "The Osteotome Technique Part 3-Less Invasive Methods of Elevating the Sinus Floor;" 1994).

The technique causes expansion of the pilot hole without further elimination of bone material, and generally compresses the bone and increases bone density, in the surgeon's favor. The technique uses a succession of conical expansion Osteotome tools having a gradual diameter escalation. The smallest caliber expansion Osteotome tool is inserted manually into the pilot hole, with pressing and rotating of the tool occurring until the desired depth is reached, or until further penetration is resisted, at which time gentle tapping using a surgical mallet on the Osteotome may cause it to reach the proper depth. Further use of successively larger Osteotome tools causes lateral compression that increases bone density and the size of the opening. The different calibers of Osteotomes may be constructed such that the initial diameter of a successively larger Osteotome is the same as the largest penetrating diameter of the previous conical Osteotome that was used, thereby providing a constant progression of increasing separation.

During the expansion of the opening, with its resulting bone compression using the succession of Osteotomes, care must be taken as to the depth of penetration by the tools, to avoid puncturing of the sinus membrane. Once sufficient expansion and compaction has occurred for the intended implant, the cortical bone layer of the inferior sinus wall (floor) may be intentionally breached using the Osteotome, while exercising due diligence to again not damage the sinus membrane. The membrane is then typically detached gently and displaced inwardly (lifted) using bone placed in the osteotomy site, which is displace upwards using the osteotome to working height. The space caused by the displacement of the membrane that had been overlying the sinus floor may then be packed with small donor bone particles using a larger diameter tool. The particles become part of the patient's jawbone during the osseointegration process. The implant is generally inserted into the new "socket" immediately, when enough bone height is present to achieve good primary fixation. If there was initially insufficient bone between the upper jaw ridge and the sinus membrane to provide adequate stability for the implant, the sinus augmentation and implant placement may need to be performed in separate procedures, being separated by the passage of several months.

There are many steps taken during the performance of this procedure during which serious damage may be caused to the patient's physiology, particularly with respect to the sinus membrane. Puncturing of the membrane is a serious complication, which may be worsened by the introduction of bone particles therein, and the contracting of a fungal infection could furthermore be fatal. In addition, when a perforation occurs, the bone particle may lead to blockage of the osteum and cause sinusitis. If membrane repair cannot be carried out, the procedure should be aborted prior to bone placement. Membrane repair during the crestal approach is very difficult to achieve.

The prior art Osteotomes have sought to improve the procedure, but are nonetheless still lacking. For example, U.S. Patent Application Pub. No. 2009/0292288 by Hung discloses that "tip members . . . with different styles and sizes" may be replaceable "by a mechanical manner such as screwing." While constituting an improvement, it does not go far enough to assist the oral surgeon seeking to perform implant surgery on a patient in a brief amount of time, and in the safest manner according to his/her own physique and preferences. The present invention improves upon the Hung application.

The various improvements offered by the present invention serve to reduce the number of Osteotomes that are required by the oral surgeon, and additionally provide new apparatus that increase safety as to preventing the perforation of the sinus membrane.

OBJECTS OF THE INVENTION

It is an object of the invention to provide an Osteotome capable of compressing bone as the diameter of a straight or tapered tip is malleted to working length.

It is a further object of the invention to provide an improved Osteotome that checks to see if the sinus floor has been infractured by attempting to inject a flow of saline solution.

It is another object of the invention to provide a means of supplying a measured amount of saline solution within an implant hole to more safely cause lifting of the schneiderian membrane.

It is a further object of the invention to provide a dual port means of controlling both the amount of saline solution delivered under the displaced schneiderian membrane, and of measuring the amount of saline solution evacuated therefrom.

It is a further object of the invention to provide a means of quickly comparing the amount of evacuated saline solution with the amount of solution originally delivered through the implant hole to raise the sinus membrane.

It is another object of the invention to provide a pressure relief valve within a saline solution delivery system for an implant hole to permit the escape of saline solution with an excessive pressure gradient that risks membrane perforation.

It is a further object of the invention to provide an improved Osteotome which is adapted to receive various geometry nozzles, to allow gentle separation of the sinus membrane.

It is another object of the invention to provide an improved bone carrier

It is another object of the invention to provide a means of measuring a specific amount of donor bone particles that are to be delivered into the region above the sinus floor and below the lifted membrane.

It is a further object of the invention to provide an improved Osteotome that utilizes a saline solution to further expand and cause lateral compression of the implant insertion pilot hole.

It is also an object of the invention to provide a means of supplying a measured amount of saline solution within an implant hole, and of porting the saline solution withdrawn therefrom into a volumetric measuring means to verify sinus membrane integrity.

It is an object of the invention to provide an improved Osteotome that reduces the number of handles required, by permitting various sized conical expansion tips to be releasably secured in a specially adapted handle.

It is another object of the invention to provide various sized handles that may be interchangeable with various sizes of conical expansion tips to serve as replaceable grippers.

Further objects and advantages of the invention will become apparent from the following description and claims, and from the accompanying drawings.

BRIEF DESCRIPTION OF THE DRAWINGS

FIG. 4A illustrates a second alternate embodiment of the interchangeable body members of the present invention, and a series of corresponding handles of differing sizes, for interchangeably receiving those body members.

FIG. 4B illustrates one of the interchangeable body members of FIG. 4A having been releasably received within a small diameter handle of FIG. 4A.

FIG. 4C illustrates one of the interchangeable body members of FIG. 4A having been releasably received within a large diameter handle of FIG. 4A.

FIG. 5B is an end view of the nozzle exit configuration of the hydration-capable tip of FIG. 5A.

FIG. 5C is an end view of an alternate nozzle exit configuration for the hydration-capable tip of FIG. 5A.

FIG. 5D is an end view of a third nozzle exit configuration for the hydration-capable tip of FIG. 5A.

FIG. 5E is an end view of a fourth nozzle exit configuration for the hydration-capable tip of FIG. 5A.

FIG. 5F is the view of FIG. 5, but having a reduction cylinder of the present invention secured over the tip for control of depth of penetration.

FIG. 5G is an enlarged detail view of the reduction cylinder of FIG. 5F.

FIG. 5H is a top view of the reduction cylinder of FIG. 5G.

FIG. 5I is an enlarged detail view of a larger sized reduction cylinder.

FIG. 5J is an enlarged detail view of a second larger sized reduction cylinder.

FIG. 5K is an enlarged detail view of a third larger sized reduction cylinder.

FIG. 5L is an enlarged detail view of a fourth larger size reduction cylinder.

FIG. 6 is the Hydrotome of FIG. 5, with the hydration port being coupled to the outlet of a syringe using a tube, and with a flow control nozzle being secured onto the tip.

FIG. 6A is an enlarged view of the tip of the Hydrotome of FIG. 6.

FIG. 14 is a top view of a bone penetration measurement device of the present invention.

FIG. 14A is a side view of the bone penetration measurement device of FIG. 14.

FIG. 15 is a side view of a bone particle delivery tool of the present invention.

FIG. 16A shows the cylindrical extension of the bone particle delivery tool initially being inserted into a first cylindrical opening of the bone penetration measurement device of FIG. 14.

FIG. 16B shows the arrangement of FIG. 16A, but with the cylinder of the bone particle delivery tool being slid to contact the side of the bone penetration measurement device of FIG. 14.

FIG. 16C shows the arrangement of FIG. 16B, but with the ring of the bone particle delivery tool being slid to contact the cylinder, and thereby set the depth of penetration of the cylindrical extension of the bone particle delivery tool, relative to the cylinder.

DETAILED DESCRIPTION OF THE INVENTION

Figure 1:
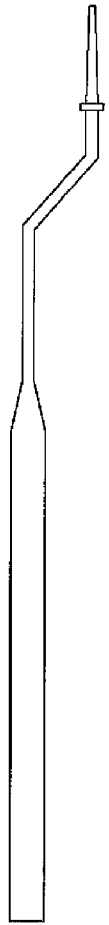
FIG. 1 is a side view of a prior art Osteotome.
Figure 2A:
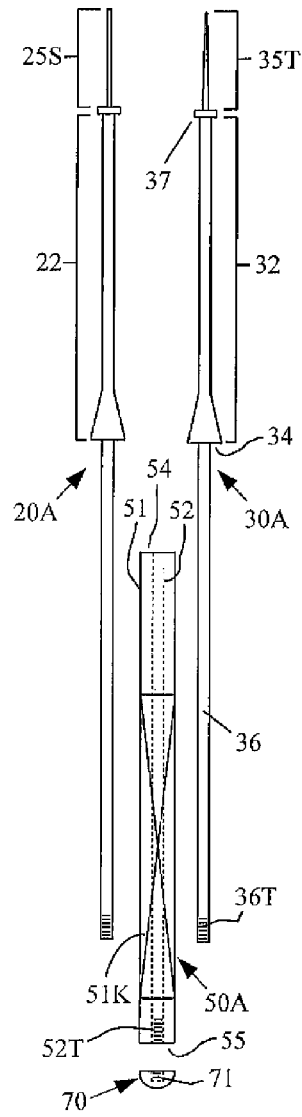
FIG. 2A illustrates a series of interchangeable body members with various size/type tips that may be releasably received within the illustrated Osteotome handle of the present invention.

FIG. 1 shows a prior art Osteotome that is usable for providing the necessary expansion and compaction of bone surrounding an implant pilot hole formed in an alveolar ridge during a Sinus Lift procedure. FIG. 2A shows a series of component parts that may be assembled to form an improved, more versatile Osteotome of the present invention. One aspect of the improved Osteotome disclosed herein is that it may comprise a series of replaceable body members with various different tips, where the body member may be releasably secured into a single handle member, to eliminate the need to procure a complete set of handles with various integral tips, as a typical set of Sinus Lift Osteotomes will often contain a set of at least 5 Osteotomes similar to the one shown in FIG. 1.

It should be noted that the support member 22/32, from which the tips extend, may be straight, as seen for the body members 20A and 30A in FIG. 2A, or they may be offset, as seen for the prior art Osteotome of FIG. 1. In addition, the tip itself may be a straight tip 25S, as seen for body member 20A, or the tip may be a tapered tip 35T, as seen for body member 30A. A typical set of Osteotomes usable for the sinus lift procedure may thus include, for example, a handle with a tip tapering from 2.2 mm to 2.7 mm, another handle with a tip tapering from 2.7 mm to 3.2 mm, a handle with a tip tapering from 3.2 mm to 3.7 mm, a handle with a tip tapering from 3.7 mm to 4.2 mm, and a handle with a tip tapering from 4.2 mm to 5.0 mm. The typical set of straight tip Osteotomes may simply comprise a series of handles having respective body members with respective tips in the form of cylinders of a specific diameter (e.g., a handle with a 2.7 mm diameter tip, one with a 3.2 mm diameter tip, a 3.7 mm tip, a 4.2 mm tip, and 5.0 mm tip).

One aspect of the Osteotomes of the present invention, as discussed above, is the possibility of interchangeability, which may therefore be directed to a more economical set of tools, as well as offering the possibility of improvements in the ergonomics of the handles through such interchangeability. As seen in FIG. 2A, the body member 30A may comprise a support member 32, from which a tip 35T may extend, and which may include a stop 37 that may be fixed thereon or may be threadably secured thereon to be adjustable. The body member 32 may terminate at a shoulder 34, from which may protrude a cylindrical shaft 36. The distal end of the shaft 36 may comprise a series of external threads 36T.

Figure 2B:
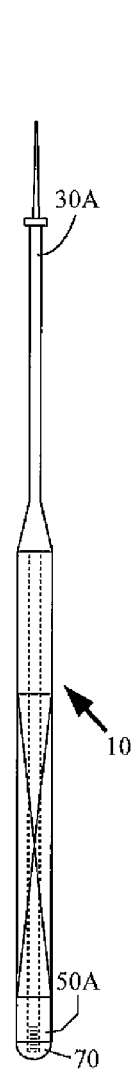
FIG. 2B illustrates one of the interchangeable body members of FIG. 2A having been releasably received within the handle of FIG. 2A.

The handle member 50A may be comprised of a graspable shaft 51, a portion of which may comprise a knurled exterior surface 51K to better facilitate handling when grasped by the oral surgeon. An orifice 52 may extend throughout handle member 50A. To releasably secure the body member 30A to the handle 50A, a portion of the orifice 52 at its distal end may comprise internal threading 52T. The shaft 36 of body member 30A may be slidably received within orifice 52 of handle member 50A, with the external threads 36T contacting and becoming threadably engaged with the internal threading 52T of the handle member, until the shoulder 34 of the body member contacts the end 54 of the handle, as seen in FIG. 2B. The shaft 36 may be of sufficient length so that when installed as just described, it may protrude from the end 55 of the handle. A cap 70 having an orifice 71 therein with internal threading 71A, may be threadably secured onto the external threads 36T of the protruding portion of the shaft 36 to form the Osteotome 10. Osteotome 10 comprises the assembly of handle member 50A, body member 30A, and cap 70, but the Osteotome could quickly be reconfigured by removing body member 30A, and replacing it with another body member having a desired tip, such as, for example body member 20A.

Figure 3A:
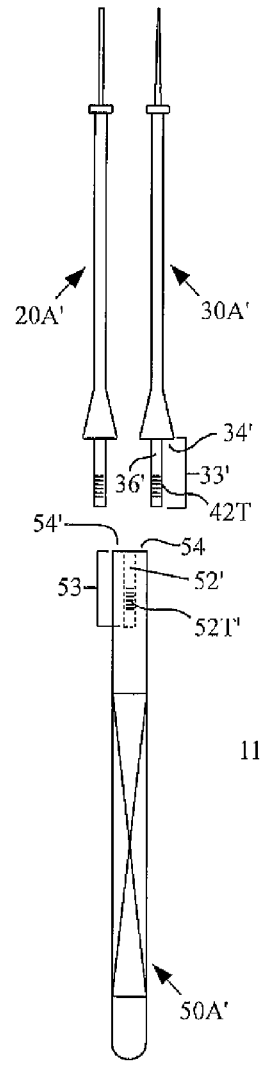
FIG. 3A illustrates an alternate embodiment of the interchangeable body members of the present invention, and the corresponding handle for releasably receiving those body members.
Figure 3B:
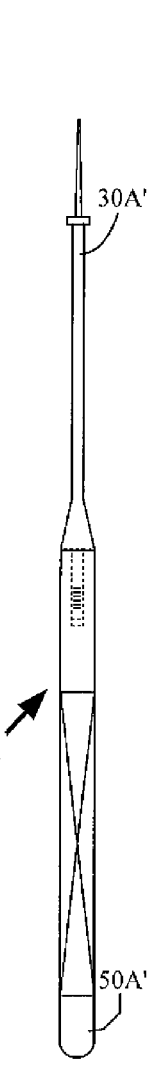
FIG. 3B illustrates one of the interchangeable body members of FIG. 3A having been releasably received within the handle of FIG. 3A.

In an alternate embodiment, seen within FIGS. 3A and 3B, the shaft 36' of body member 30A' may only extend to a length 33'. Also, the orifice 52' in the handle may extend to depth 53', which may be slightly longer than the length 33 of shaft 36', and which may contain internal threading 52T' therein. The shaft 36' may be threadably received within orifice 52' to form Osteotome 11.

A further aspect of the interchangeability of the improved Osteotome of the present invention is shown by FIGS. 4A-4C. To accommodate an easily and more quickly interchangeable series of body members having various tips, with a handle, the internal and external threading of the handle member 50 and body members 20A, 20A', 30A, and 30A', may be eliminated, and a simple friction fit therebetween may instead be used.

Alternatively, rather than a simple friction fit, an easily interchangeable series of body members and handles that provide positive retention while still enabling releasable connectivity therebetween, may be provided through the use of a detent arrangement. This is illustrated in FIG. 4A for body members 40A, 40B, 40C, 40D, and 40E, and for the corresponding handles 60A, 60B, and 60C. The detent may comprise a pair of opposingly biased spherical balls, 48i/48ii, being retained within a transverse orifice on the shaft 46 of the body member, which, when mated with one of the corresponding handles, are thus biased into, and releasably received within, an annular groove 68 within the orifice 62 of the handles 60A-60C. The provision of several handles having different sizes and/or different shapes (e.g., different diameter cylinders and/or with thumb/finger impressions) provides the oral surgeon with increased versatility in customizing the set of tools to his/her own individual hand size/grip, or individual preference for a particular sized tip (e.g., 2.7 mm diameter tip versus a 5.0 mm tip), etc. FIG. 4B illustrates one possible combination of the components of FIG. 4A, where the body member 40A having the smaller tip (2.2 mm tapering to 2.7 mm) is used on the smaller diameter handle 60A. FIG. 4C illustrates another possible combination of the components of FIG. 4A, where the body member 40E having the larger tip (4.2 mm tapering to 5.0 mm) is used on the larger diameter handle 60C. Any one of the body members of FIG. 4A may be interchangeably used on any handles illustrated therein. Also, although FIG. 4A illustrated three different sized handles, other combinations of handles may be included in a set to increase interchangeability. For example, there may any number of different diameter handles, as well as a series of handles having different hand impressions thereon instead of, or in addition to, knurling, to improve the grip that may be obtained by the oral surgeon. A flange 46F or other key-type feature, as seen for body member 40A in FIG. 4A, may be received in a correspondingly shaped recess $60C_R$ or other key-way type feature in the handle 60C, to prevent counter-rotation of the body with respect to the handle, and may be used on any of the embodiments disclosed herein.

Figure 4D:
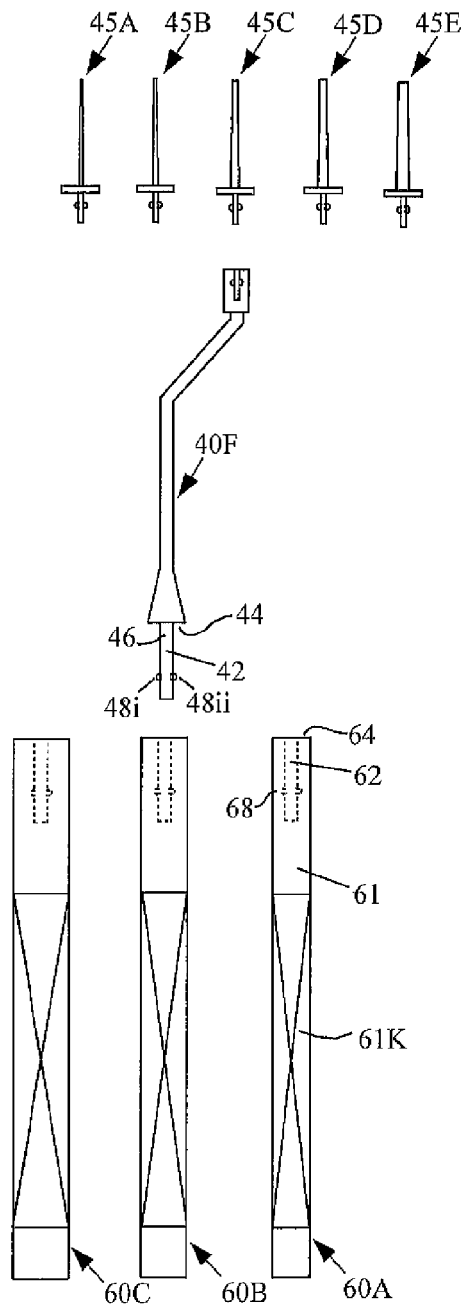
FIG. 4D illustrates a third alternate embodiment of the interchangeable body members of the present invention, having a series of corresponding handles of differing sizes, for interchangeably receiving those body members, and with the body members being capable of interchangeably receiving different tips.
Figures 4E, 4F:
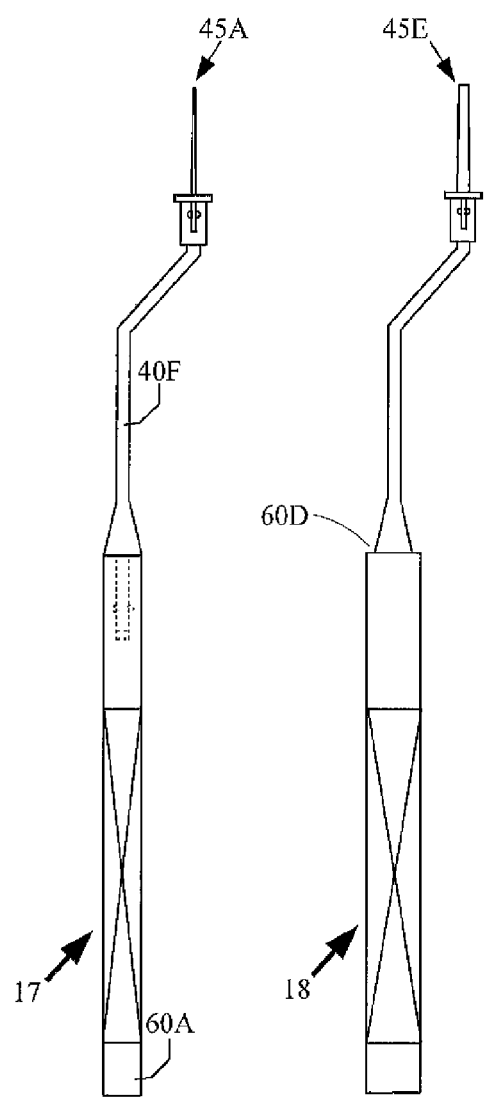
FIG. 4E illustrates one of the interchangeable body members of FIG. 4D having been releasably received within a small diameter handle of FIG. 4D, and with the smallest of the tips being releasably received within the body member.
FIG. 4F illustrates one of the interchangeable body members of FIG. 4D having been releasably received within a large diameter handle of FIG. 4D, and with the largest of the tips being releasably received within the body member.

Yet another aspect of the interchangeability of the improved Osteotome of the present invention is shown by FIGS. 4D-4F. To accommodate an easily and more quickly interchangeable series of tips, the detent arrangement described above may also be used between an interchangeable tip and the body member. This is illustrated in FIG. 4D for tips 45A, 45B, 45C, 45D, and 45E, each of which may be interchangeable with another of these tips, through being releasably received by a body member 40F, which may be interchangeably received by corresponding handles 60A, 60B, and 60C. FIG. 4E illustrates one possible combination of the components of Figure D, where the body member 40F has the smallest interchangeable tip 45A (2.2 mm tapering to 2.7 mm) releasably secured therein, and where the body member 40F is releasably secured within the smaller diameter handle 60A. FIG. 4F illustrates another embodiment for the components of FIG. 4A, comprising an integrally formed body member/handle 60D, having the larger tip (4.2 mm tapering to 5.0 mm) being releasably received therein.

Figure 5:
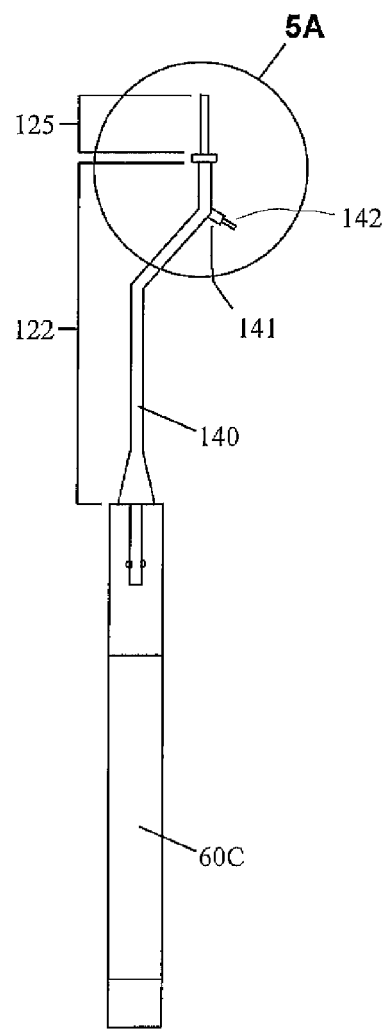
FIG. 5 illustrates a first embodiment of the Hydration Osteotome- Hydrotome- of the present invention, with a body member having a hydration-capable tip being releasably secured to a handle of the present invention.

A further aspect of the present invention is shown beginning within FIG. 5. The Osteotomes disclosed herein, whether for the straight or for the offset body members, may also incorporate a hydration port, and a conduit throughout a select portion of the tool, forming a first embodiment of a Hydrotome of the present invention. The body member 140, shown being releasably received within handle 60C in FIG. 5, may include an offset (joggled) body member 122, from which may extend a tip 125. The tip 125 may be a straight tip or a tapered tip that may be used for the lateral compression and increases in bone density occurring through the use of a succession of tools exhibiting a diameter escalation as previously described.

Figure 5A:
FIG. 5A is an enlarged view of the hydration-capable tip of FIG. 5.
Figure 5A:
Figure 5A:
Figure 5A:
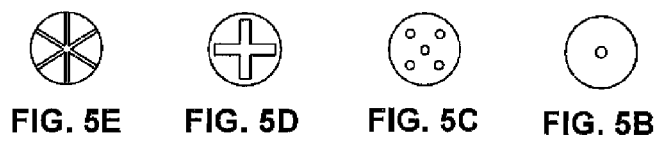
Figure 5A:
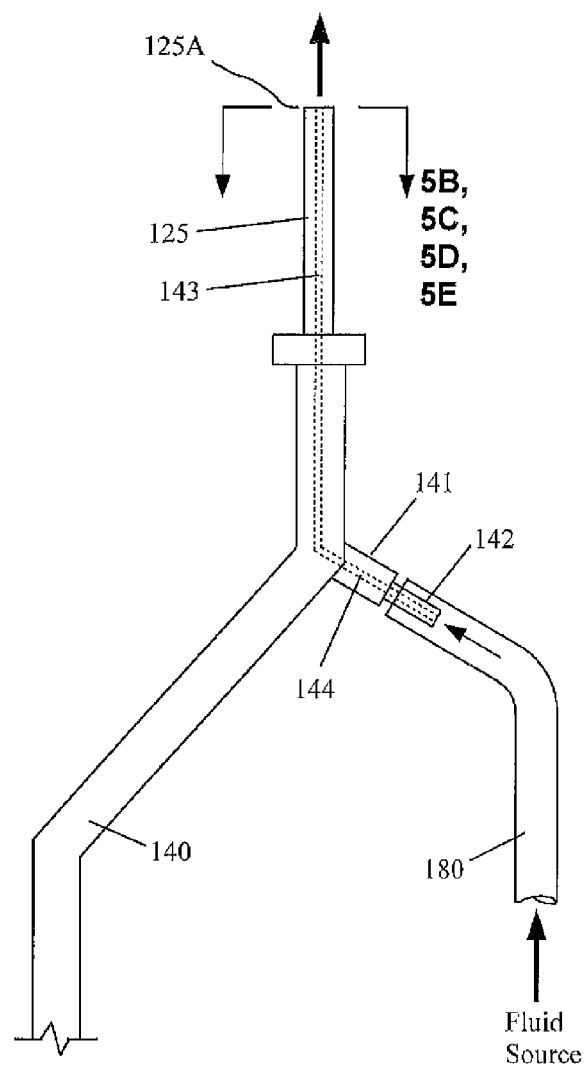

At a convenient location on the body member 122, preferably being in proximity to the upper bend, a port 141 may extend away from the bend and terminate in a connector 142. The body member 122 may also comprise a conduit 143 (FIG. 5A) that may begin at the end 125A of tip 125, and may extend into the body member 140, where it may be coupled to a conduit 144 within the port 141 that terminates at the end of the connector 142. The connector 142 may be a threaded coupling to receive the corresponding connector for a hose that may supply saline solution under pressure from a pool of the solution. The connector 142 may alternatively be just a cylindrical extension of the port 141, upon which a tube may be secured, through the use of a friction fit therebetween, or through the use of adhesive, or a clamp, etc.

Having a complete set of Hydrotomes with various sized tip diameters being so constructed, may enable an oral surgeon to carefully breach the cortical bone layer using the largest caliber tool required to create a suitably sized "socket" for the desired implant, and to thereafter carefully detach the Schneiderian membrane and cause lifting of the membrane through the calibrated flow of saline solution therein. FIG. 5B shows the conduit 143 terminating in a nozzle opening being a single, centered circular opening. FIG. 5C illustrates a distributed multi-opening nozzle configuration that may serve to more evenly distribute the pressure induced upon the membrane either during or immediately subsequent to the tool causing the up-fracture of the remaining 1 mm of the cortical bone layer, to provide for gentler lifting of the membrane. The cruciform nozzle opening of FIG. 5D, and the hexaform-shaped nozzle opening of FIG. 5E may also further serve to more evenly distribute pressure and reduce localized stress to the membrane to prevent injury thereto during separation and lifting.

The depth of penetration into the implant socket, of the tip of any of the Hydrotomes herein disclosed may be controlled by the aforementioned stop 37 that may be threadably secured upon the tip to be adjustable thereon. FIG. 5F illustrates an alternative Hydrotome having a stop 137 being fixed upon the tip, and with a diameter 137D of a reduction cylinder 137A (FIGS. 5F-5H) being received on the tip in a friction fit to abut the stop 137. The reduction cylinder 137A thereby serves to limit the depth of penetration of the tip, according to the height 137H of the cylinder. The reduction cylinders shown in FIGS. 5I-5L may be comprise varying heights (e.g., 237A, 337A, 437A, and 537A) which may replace the reduction cylinder 137A at the appropriate point in the procedure to modify the depth of penetration of the tip as needed.

A further embodiment of the Hydrotome of the present invention is shown by the Hydratome arrangement 14 of FIG. 6. To provide for more deliberate and/or sequential delivery scheme for the saline solution, a special Hydrotome tool may comprise a body member with a tip that is adapted to releasably receive a separate, interchangeable nozzle member. FIG. 6 shows a nozzle member 250A being releasably received upon the tip 225 of the body member 240. The nozzle member 250A may be releasably retained upon the tip using a friction fit, or threading, or a detent arrangement similar to the one used for the mounting of the body member 240 within the handle 60C. An O-ring member 252 or even a gasket may be used to seal the connection between the nozzle 250A and the tip of the body member 240 to prevent leakage therefrom. A conduit 253 in the nozzle member 250A may thus be in fluid communication with the conduit 243 of the body member 240.

Figure 8A:
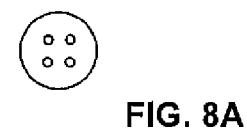
FIG. 8A is a top view of the flow control nozzle of FIG. 8.
Figure 8:
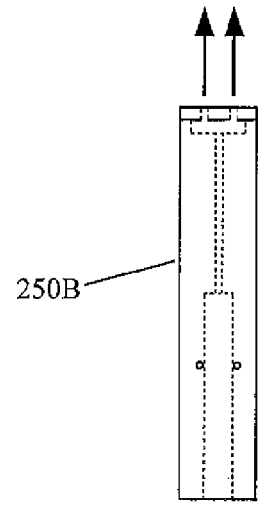
FIG. 8 is an enlarged side view of a second flow control nozzle being usable on the tip of the Hydrotome of FIG. 6.
Figure 10A:
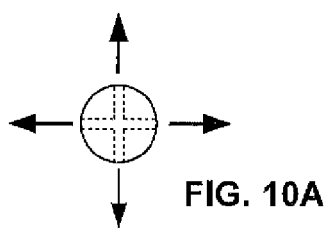
FIG. 10A is a top view of the flow control nozzle of FIG. 10.
Figure 10:
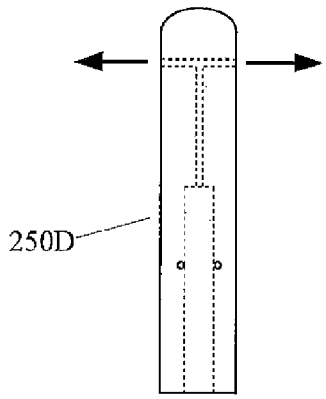
FIG. 10 is an enlarged side view of a fourth flow control nozzle being usable on the tip of the Hydrotome of FIG. 6.
Figure 7A:
FIG. 7A is a top view of the flow control nozzle of FIG. 7.
Figure 7:
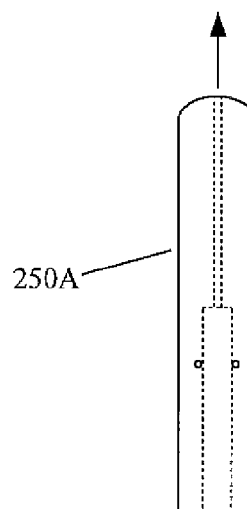
FIG. 7 is an enlarged side view of the flow control nozzle of FIG. 6.

As seen in FIG. 7-10, a series of nozzles may be used to delicately lift and separate the Schneiderian membrane from the sinus floor. Initially, the nozzle head 250A may be used during or immediately after the up-fracture of the cortical layer, with the delivery of fluid through the single opening in the rounded upper surface of the head causing local separation of the membrane at the site of the up-fracture, and with transmission of the fluid positively signaling to the practitioner that upfracture has occurred. Once upfracture is confirmed, the nozzle head 250A may be replaced by nozzle head 250B, which is adapted to provide a more dispersed delivery of the saline solution, and may comprises four or preferably five or more delivery orifices for the saline solution, which may be evenly distributed about the face of the head, as seen in FIG. 8A. The delivery of saline solution from the top of nozzle head 250B may also be accomplished by using a cruciform nozzle opening similar to that of FIG. 5D, or the hexaform-shaped nozzle opening of FIG. 5E. To more safely lift the membrane and impose less of a risk of a perforation therein, the nozzle head may preferably have a plurality of openings, which may serve to increase the number of separate streams of saline solution that are exerting a force upon the membrane to cause it to lift.

Figure 9A:
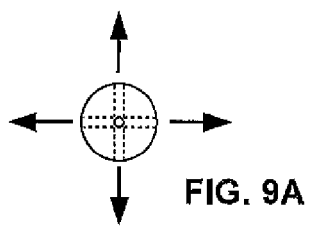
FIG. 9A is a top view of the flow control nozzle of FIG. 9.
Figure 9:
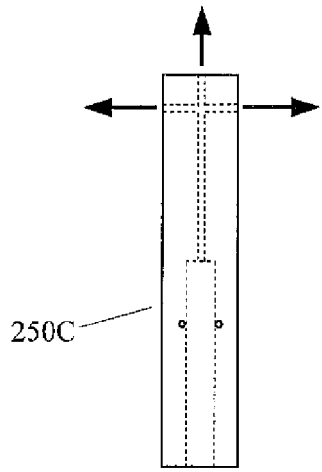
FIG. 9 is an enlarged side view of a third flow control nozzle being usable on the tip of the Hydrotome of FIG. 6.

As the Hydrotome progresses further to be just above the sinus floor, nozzle head 250B may be replaced with nozzle head 250C. As seen in FIGS. 9 and 9A, nozzle head 250C may comprise one or more exit orifices in the top of the head, but may also preferably comprise a series of exit orifices on the side of the nozzle head to provide for lateral delivery of the saline solution, which may be used to apply a separation force to further separate the membrane at the lateral location at which it still adheres to the bone. Thereafter, or in place of having used the nozzle head 250C, a nozzle head 250D may be used. The nozzle head 250D may have a rounded top surface without any exit orifices thereon, as only its side may have a series of exit orifices (3, 4, or more) to provide for lateral delivery of the saline solution and separation of the membrane. The top surfaces of nozzles 250B and 250C may also be rounded.

Another aspect of the present invention that is illustrated within the arrangement 14 of FIG. 6 is that the introduction of saline solution may be accomplished through the use of a syringe 290 that uses, in place of a needle, a tube 280 to couple its outlet opening with the connector 242 of the port 241 of the Hydrotome. This arrangement 14 permits the oral surgeon to introduce into the region above the sinus floor and below the sinus membrane, only a particular measured amount of saline solution that is calibrated in accordance with the specific geometry of the patient's physiology (age/jaw dimensions) and the degree to which the practitioner needs to lift the membrane.

To begin the process, the oral surgeon may first draw saline solution into the syringe 290, and then, with the nozzle head being elevated, he/she may advance the plunger to release excess saline solution out of the exit orifices until only the desired amount of saline solution 299 remains trapped within the syringe for delivery into the maxillary sinus, as indicated by the plunger's position relative to the graduated scale. Saline solution will also remain within the tube 280, as well as the conduit of the body member of the Hydrotome. The nozzle head used for delivery of the saline solution may then be urged into the implant socket using handle 60C, to be securely received therein so as to form a fluid-tight interface. The plunger of the syringe 290 may then be smoothly advanced to introduce the desired amount of solution above the sinus floor to cause the requisite separation of the membrane. In this embodiment, it is anticipated that the volume of fluid being introduced between the sinus floor and the membrane would be primarily responsible for causing the lifting of the membrane.

Figure 11:
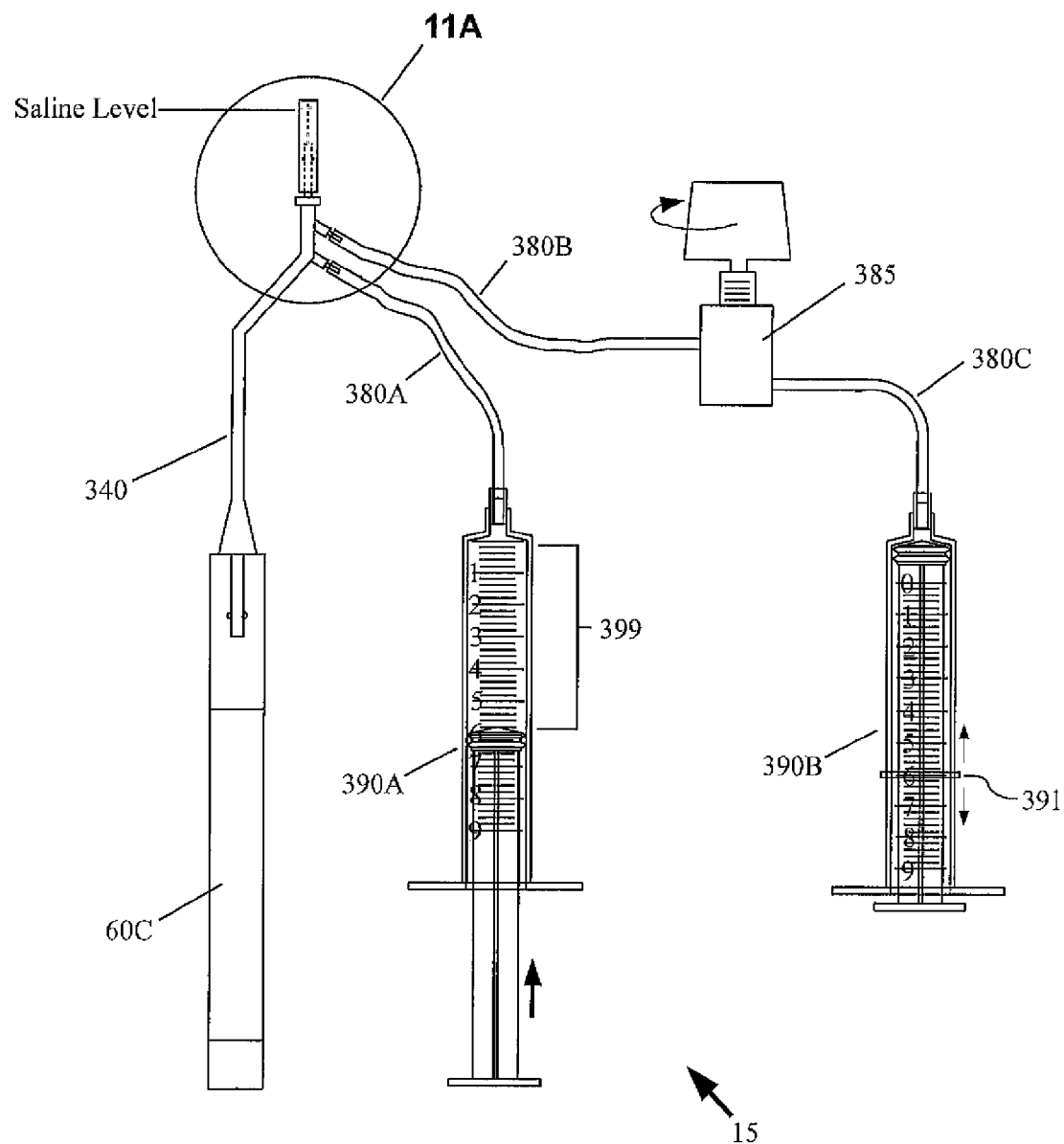
FIG. 11 is a second embodiment of the Hydration Osteotome of the present invention, having a hydration port being coupled to the outlet of a first syringe using a tube, having a drain port being coupled to a second syringe with a valve therebetween, and with a flow control nozzle being secured onto the tip of the Hydration Osteotome.

A further embodiment of the Hydrotome of the present invention is shown by the arrangement 15 of FIG. 11. To better inform the oral surgeon that the sinus membrane has not been perforated, which may result in the drainage of a distinct or indistinct portion of the saline solution from the maxillary sinus into the middle meatus of the nose, the arrangement 15 may provide for both the measured delivery of saline solution, as well as the measured evacuation of the solution therefrom. The Hydrotome arrangement 15 may be the same as arrangement 14, except that in addition to a first port 341A and a first connector 342A, it may further include a second port 341B and second connector 342B (FIG. 11A) that may receive a second tube 380B that is coupled to an inlet of a valve 385. Another tube 380C may couple the outlet of the valve 385 to a second syringe 390B.

The Hydrotome arrangement 15 may be utilized in several different ways in order to measure the saline solution evacuated from the maxillary sinus. In one set-up, the valve 385 should be rotated as shown to be closed. Next, the saline solution may be initially introduced into the Hydrotome arrangement 15 similar to that of the arrangement 14, in that the solution may be drawn into syringe 390A to be proximate to the top of the nozzle head (see FIG. 11A). This should be accomplished with the valve being closed, so that tube 380B would be filled with saline solution, but tube 380C would be empty. To receive saline solution within tube 380B and not 380C, the valve may need to initially be opened and the plunger of syringe 390B may be withdrawn to draw the solution into both tubes 380E and 380C. Thereafter, the valve 345 may be closed, the connection of tube 380C to the valve 345 may be loosened to permit the solution to flow out from tube 380C and out from syringe 390B, after which tube 380C may be reconnected to valve 345.

Figure 12:
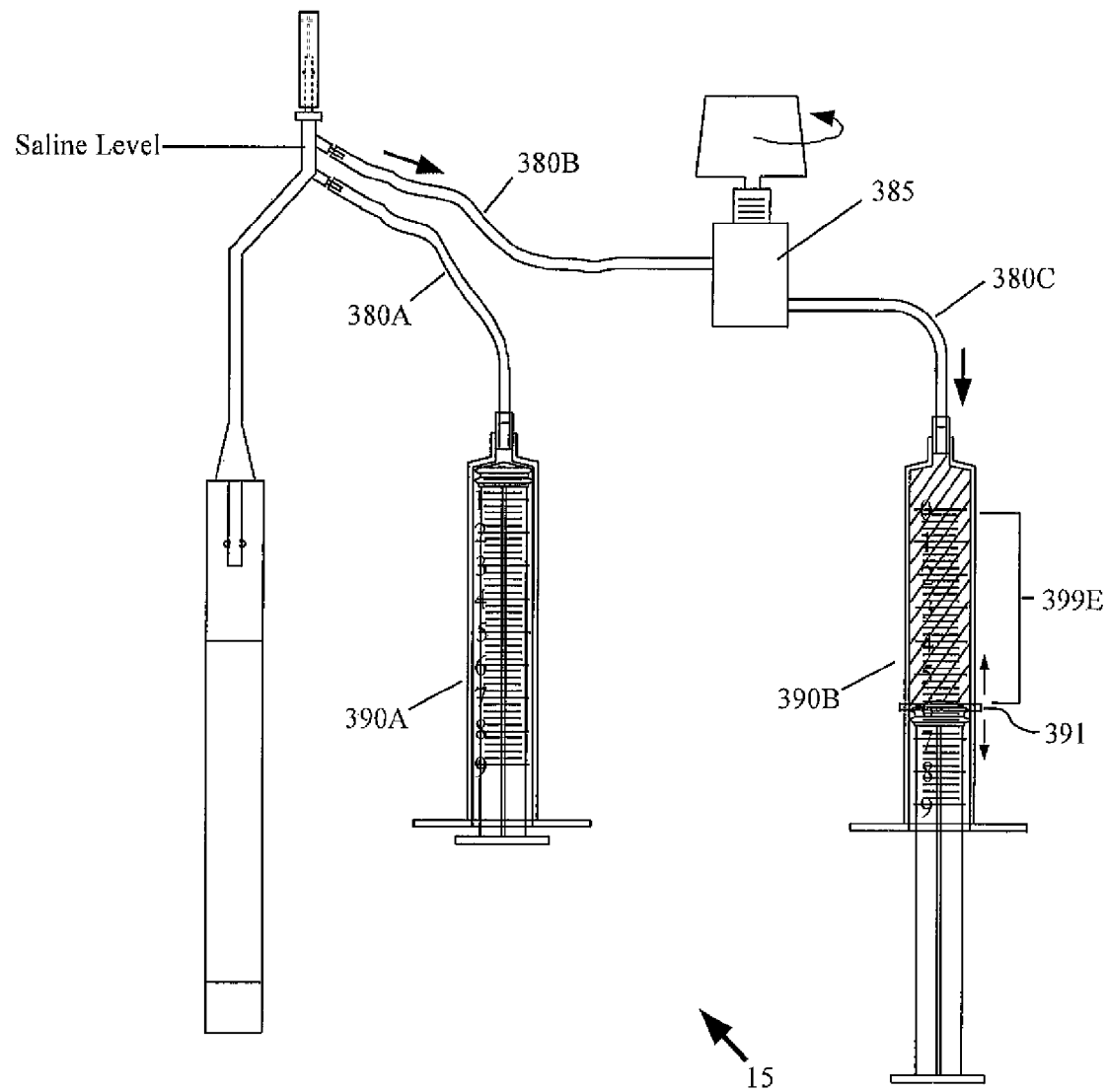
FIG. 12 is the Hydration Osteotome arrangement of FIG. 11, but after the plunger of the first syringe was actuated to deliver the saline solution, and after the valve was opened to allow evacuation of the saline solution by the second syringe.

In using the Hydrotome arrangement 15, the oral surgeon may urge the nozzle head used for delivery of the saline solution into the implant socket, using handle 60C, to be securely received therein so as to form a fluid-tight interface. The plunger of the syringe 390A may then be smoothly advanced to introduce the desired/measured amount of solution 399 above the sinus floor, to cause the requisite separation of the membrane. In this embodiment, it is anticipated that the volume of fluid being introduced between the sinus floor and the membrane would again be primarily responsible for causing the lifting of the membrane. With the syringe 390A being maintained in the depressed position that caused expulsion of the saline solution from its tube, as seen in FIG. 12, and with the membrane having thus been lifted, the valve 385 may then be opened, and the plunger of syringe 390B may withdrawn to evacuate the saline solution from above the patient's sinus floor. If none of the measured amount of saline solution has been lost through a perforated membrane, the evacuated saline solution 399E received between the graduated marks of syringe 390B should approximately match the amount of saline solution 399 that had been expelled from syringe 390A.

Figure 11A:
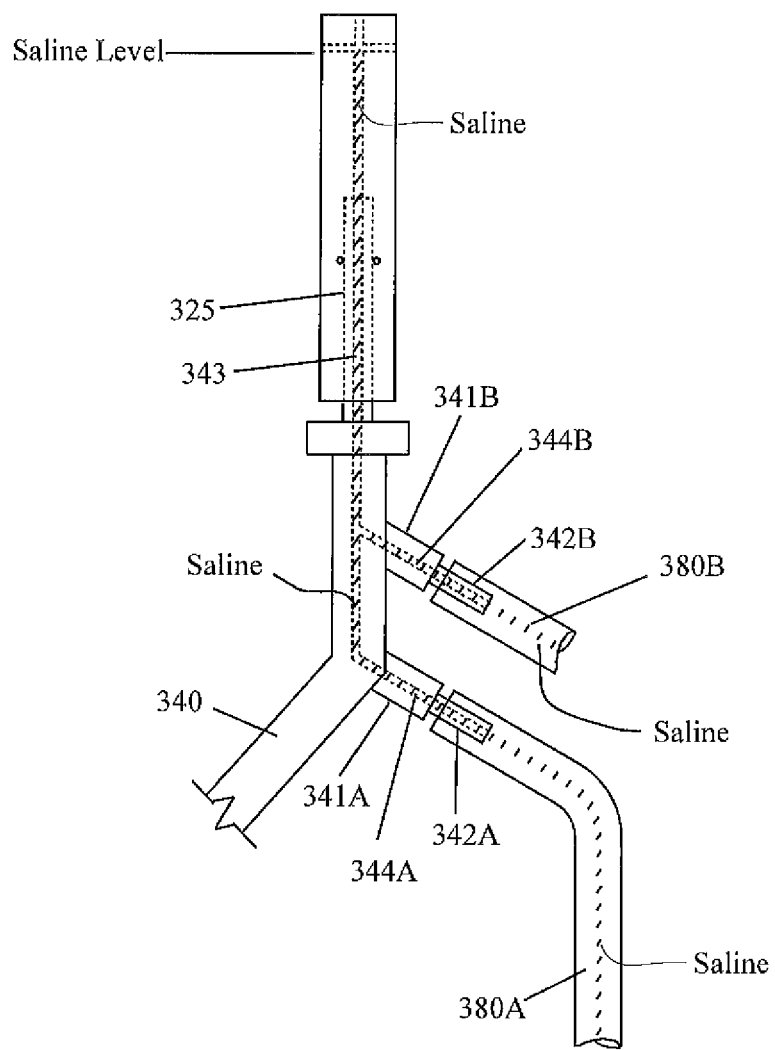
FIG. 11A is an enlarged view of the Hydration Osteotome of FIG. 11, showing the level of saline solution contained therein.

Note that the numbering for the graduated marks of syringe 390B do not begin at the top of its tube, as the volume corresponding to this displacement may be calibrated to account for the amount of saline solution that had initially been contained within tube 380B and the amount that had initially occupied the nozzle head and the portion of conduit 343 above the juncture with conduit 344B (see FIG. 11A). Thus, the amount of saline solution actually evacuated from above the sinus floor would be measured downward beginning with the graduated marking labeled as zero. If the sinus membrane had been punctured, the amount of saline solution evacuated and now contained within syringe 390E would be measurably less.

To assist the oral surgeon as to the expected amount of saline to be evacuated from above the sinus floor, the syringe 390B, as seen in FIGS. 11 and 12, may comprise a colored ring 391 that is slidably received upon the tube of the syringe. When the oral surgeon has determined the amount of saline solution needed for raising of the sinus membrane, and has drawn it into syringe 390A, e.g., 6 ml for the syringe in FIG. 11, the surgeon may then slide the ring 391 on syringe 390B to the 6 ml graduate mark as a visual reminder of the amount expected to be later evacuated. Alternatively, the syringe 390A may have the slidable ring 391 slidably mounted thereon, which may be moved to the location indicating the amount of saline solution that will be introduced above the patient's sinus floor using that syringe. The surgeon may thereafter perform the evacuation of saline solution into syringe 390B, and then compare the amount of saline therein with the position of ring 391 on syringe 390A. Alternatively, a ring 391 could be used on both syringe 390A and syringe 390B.

Figure 12A:
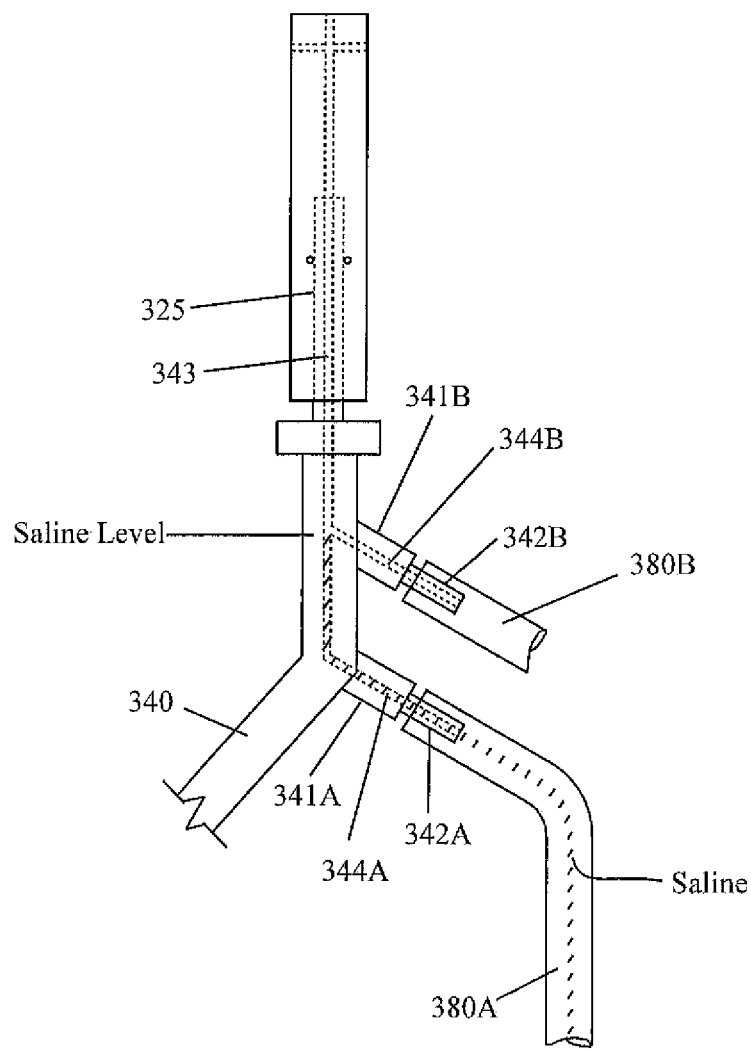
FIG. 12A is the view of FIG. 11A, but showing an alternate level of saline solution in the Hydrotome, prior to it being introduced into the implant socket.

It should be noted that different positioning of the ports may be accommodated, so that, for example, port 341A and port 341B may be at the same height. In addition, other arrangements for the initial and final saline solution levels may be utilized. For example, initially, there need not be any fluid in tube 380B (see FIG. 12A), so that no shift in the graduated markings would be necessary for syringe 398B. However, in order to prevent entry of saline solution therein during its expulsion from syringe 390A, which is intended for lifting the sinus membrane, a means of preventing fluid from entering therein is necessary. Rather than adding another flow control valve at that location, the functionality of valve 385 in such an arrangement may be incorporated directly into the body member 340. During lifting of the membrane, the valve may block flow towards syringe 390B, and during evacuation, the valve would only permit flow towards syringe 390B and prevent backflow towards syringe 390A.

Figure 13:
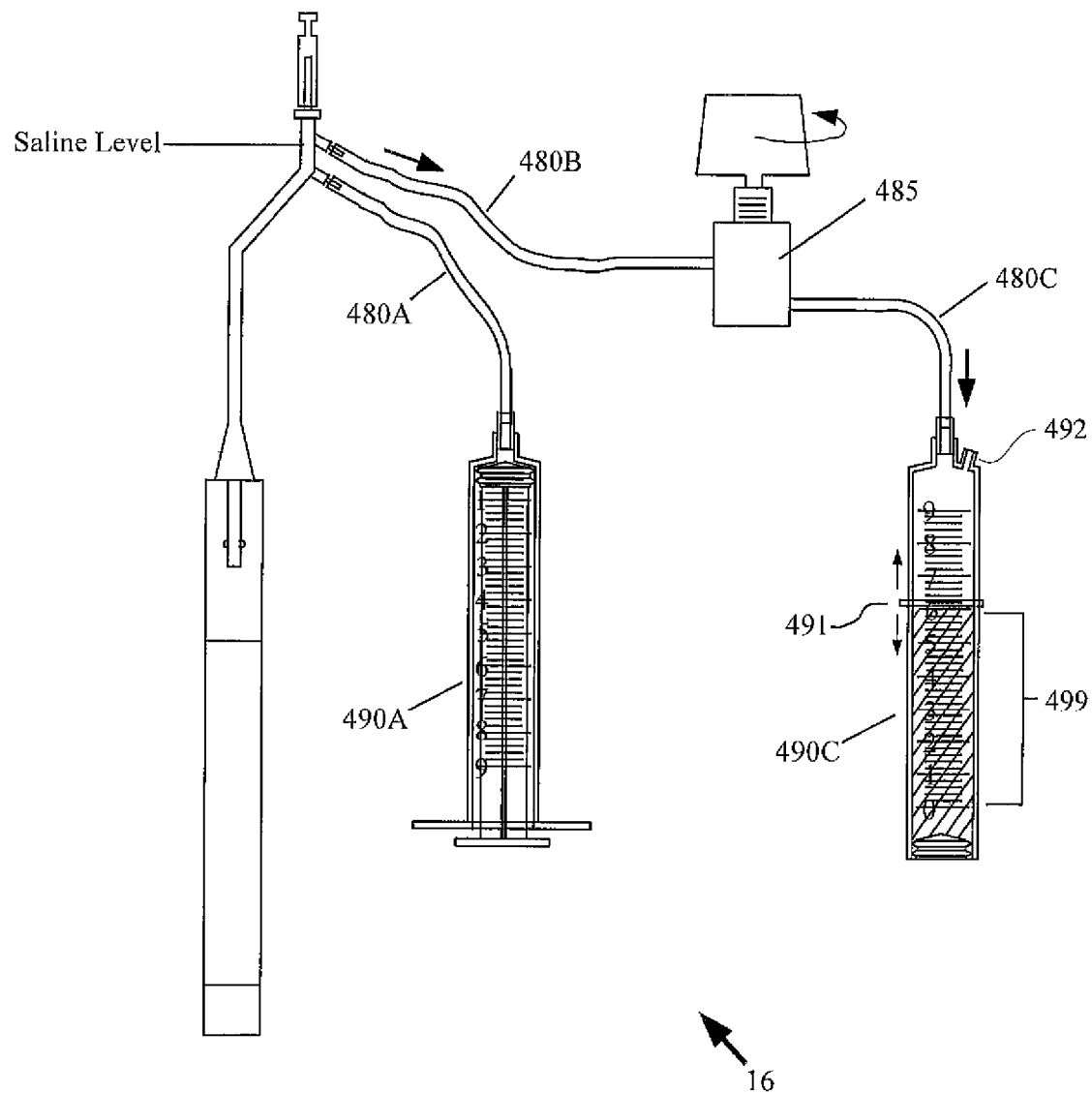
FIG. 13 is a third embodiment of the Hydration Osteotome of the present invention, having a hydration port being coupled to the outlet of a first syringe using a tube, having a drain port being coupled to a graduated cylinder with a valve therebetween, and with a flow control nozzle being secured onto the tip of the Hydration Osteotome.

FIG. 13 illustrates a Hydrotome arrangement 16 that is similar to arrangement 15, except that rather than using a syringe for evacuation of the saline solution from above the sinus floor of the patient, a graduated cylinder 490C having a sealed bottom may instead be used to allow the saline solution to normally drain therein. The top of the graduated cylinder 490C may comprise a vent 492 to allow air to escape, as the saline solution enters the cylinder. Note that the saline solution would thus flow to the bottom of the cylinder 490C, and therefore the graduated marks begin with the "zero" level being elevated from the bottom, to again be calibrated to account for the amount of saline solution that had initially been contained within tube 380B and the amount that had initially occupied the nozzle head and the portion of conduit 343 above the juncture with conduit 344B (see FIG. 11A).

It should also be noted that valve 385 in any of the arrangements may also function as a pressure relief valve. If the oral surgeon encounters a problem with the lifting of the patient's sinus membrane, continued application of increasing fluid pressure from syringe 390A may inadvertently cause a tear in the membrane. To avoid this possibility, and of relying upon the surgeon to be cognizant of the precise amount of pressure being exerted upon the syringe, the valve may be adapted to open upon reaching a certain pressure, to prevent excessively high pressure from being exerted upon a stuck membrane, which may result in the formation of such a tear.

FIGS. 14 and 14A illustrate two views of a bone penetration measurement device 500 and a bone delivery tool 520. The device 500 may be constructed to permit setting up of the bone delivery tool 520 for insertion of bone particles above the patient's sinus floor.

The measurement device 500, as seen in FIGS. 14 and 14A, may comprise a block member 505 having at least a first cylindrical opening 502, which may have an axis positioned along a graduated measuring scale 501 that be secured to a side of the block member 505, or be inset therein.

The bone particle delivery tool 520, as seen in FIG. 15 may comprise a handle member 521 that may have a cylindrical plunger or extension 522 that terminates at a free-standing end 522A. A ring 524 may be disposed upon cylindrical extension 522 with a friction fit therebetween so as to render the ring slidable with respect to the cylindrical extension, with the application of a slight amount of force. A hollow cylinder 523 may be freely slidable upon cylindrical extension 522.

The bone delivery tool 520 may be usable with the measurement device 500, to ensure the delivery of bone particles above the sinus floor of the patient, without risking excessive penetration therein by a bone carrier. First, the oral surgeon may measure the depth of the bone into which the implant socket has been formed, either using x-rays or by using a measurement tool. As an example, it will be assumed that the surgeon measured the bone depth to be 8 mm. As seen in FIG. 16A, the cylindrical extension 522 of the bone delivery tool 520 may then be inserted into the first cylindrical opening 502, until its end 522A reaches the 8 mm mark on the graduated scale 501. Next, the freely moveable cylinder 523 may be advanced until it contacts the side of the block member 505, as seen in FIG. 16B. Then a force may be applied to the ring 524 to cause it to be advanced toward the cylinder 523 until it contacts the cylinder.

Figure 17A:
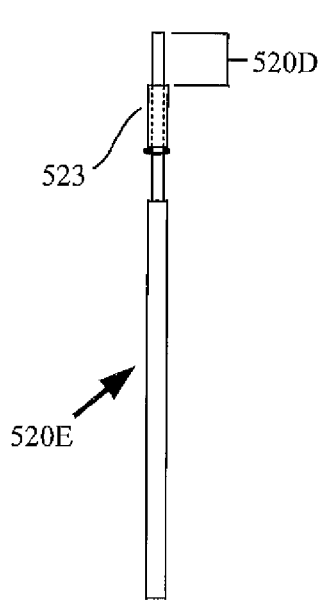
FIG. 17A shows the bone particle delivery tool of FIG. 16C, after removal from the bone penetration measurement device.
Figure 17B:
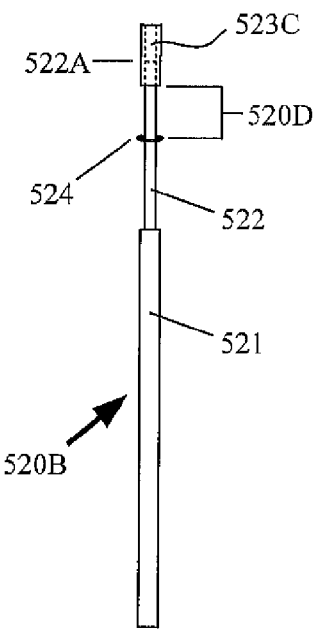
FIG. 17B shows the bone particle delivery tool of FIG. 17A, after the free-standing end of the cylindrical extension has been withdrawn to be within the cylinder, so that donor bone particles may be loaded into the cavity formed therein.
Figure 18:
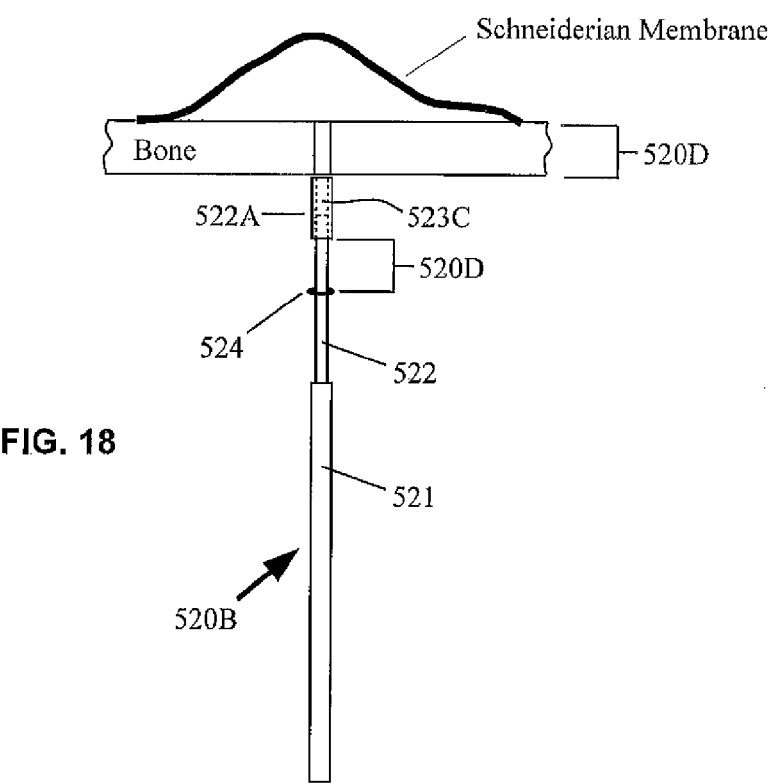
FIG. 18 shows the bone particle delivery tool of FIG. 17B being placed against the patient's bone, to be in-line with the implant socket, illustrating that the depth of penetration by the cylindrical plunger member will not be greater than the depth of the patient's bone.

The bone delivery tool may be removed from the measurement device 500, and may appear as the delivery tool 520E, as seen in FIG. 17A. The end 522A of the cylindrical extension 522 of handle 521 may protrude from the end of the cylinder 523 by an amount 520D that in this case will be 8 mm just now set through the use of the measurement device 500. The handle 521 may be backed away from the cylinder 523 to form a cylindrical cavity 523C therein, between the end of the cylinder 523 and the end 522A of the cylindrical extension 522 of the handle 521. The oral surgeon or his/her assistant may then place a load of donor bone particles within the cavity 523C. The bone filled delivery tool 520B of FIG. 17B is then ready to introduce the bone particles through the implant socket to be above the sinus floor. As seen in FIG. 18, the cylinder 523 of the delivery tool 520B may then be placed against the bone, to be in-line with the implant socket. The handle may then be advanced to cause the free-standing end 522A of cylindrical extension 522 to push the bone particles from within the cavity 523C, into the socket, and above the membrane. The depth of penetration by the cylindrical extension 522 will be limited by the ring 524 that was set to limit the amount 520D that it may extend beyond the cylinder to be 8 mm, and thus match the depth of the bone at the implant socket location.

The examples and descriptions provided merely illustrate a preferred embodiment of the present invention. Those skilled in the art and having the benefit of the present disclosure will appreciate that further embodiments may be implemented with various changes within the scope of the present invention. Other modifications, substitutions, omissions and changes may be made in the design, size, materials used or proportions, operating conditions, assembly sequence, or arrangement or positioning of elements and members of the preferred embodiment without departing from the spirit of this invention.

I claim:

1. An osteotome comprising:
a body, said body comprising:
a support portion;
a tip portion, said tip portion extending from a first end of said support portion and terminating in a free end; said tip portion comprising a first conduit configured to begin proximate to said free end of said tip portion and to extend into said support portion; said first conduit configured to terminate at said free end of said tip portion in an opening; said tip portion comprising means for interchangeably securing any one of a plurality of tip members to said tip portion; and
a hydration port, said hydration portion comprising a hydration conduit, said hydration conduit configured to be in fluid communication with said first conduit, and said hydration port configured to releasably couple a hose thereto, for the hose to be in fluid communication with said hydration conduit;
a first tip member having a first end and a second end, said first tip member comprising an orifice beginning at said second end of said first tip member and extending a portion of the way to said first end of said first tip member; said first tip member comprising a tip conduit configured to be in fluid communication with said orifice, and configured to terminate in an opening at said first end of said first tip member; said first tip member further comprising a plurality of radial conduits, each in fluid communication with said tip conduit, and configured to terminate at respective side openings at a side surface of said first tip member, in proximity to said first end of said first tip member; an axis of each of said plurality of radial conduits a configured to radiate from the same point of origin, to be generally coplanar; wherein said orifice of said first tip member is configured to releasably receive said tip portion of said body therein, to releasably mount said first tip member to said body with said means for interchangeably securing; and
a handle portion.

2. The osteotome according to claim 1 wherein said tip member further comprises a seal means, said seal means configured to for releasably sealing said tip member with respect to said tip portion.

3. The osteotome according to claim 1 wherein said first end of said tip member comprises a conical surface.

4. The osteotome according to claim 1 further comprising a syringe and a hose, said, syringe comprising a barrel with graduated markings thereon, and a plunger slidably disposed within said barrel; a first end of said hose being coupled to an outlet opening of said barrel, and a second end of said hose being coupled to said hydration port, for said barrel of said syringe to be in fluid communication with said orifice of said tip member.

5. The osteotome according to claim 1 wherein said side surface of said tip member comprises a cylindrical surface; and where said plurality of radial conduits are equally spaced radially.

6. The osteotome according to claim 1 wherein said opening proximate to said first end of said tip member comprises an opening selected from the group of openings consisting of: a single, centered circular opening on said first end of said tip member; a plurality of circular openings on said first end of said tip member; a cruciform shaped opening on said first end of said tip member; and a hexaform-shaped opening on said first end of said tip member.

* * * * *